United States Patent [19]
Yeh et al.

[11] 3,959,382
[45] May 25, 1976

[54] METHOD FOR REACTIVATING PALLADIUM CATALYSTS

[75] Inventors: Chuen Y. Yeh, Succasunna; Harry E. Ulmer, Morris Township, both of N.J.

[73] Assignee: Allied Chemical Corporation, New York, N.Y.

[22] Filed: Nov. 26, 1974

[21] Appl. No.: 527,468

[52] U.S. Cl. .......................... 260/586 P; 252/411 R; 252/411 S; 260/468 R; 260/514 R; 260/611 R; 260/617 R; 260/631 H
[51] Int. Cl.² .................. C07C 45/00; B01D 15/06
[58] Field of Search ............. 252/411 R, 411 S, 472, 252/DIG. 18; 260/586 P, 617 R, 611 R, 514 R, 468 R, 631 H

[56] References Cited
UNITED STATES PATENTS

| | | |
|---|---|---|
| 2,692,240 | 10/1954 | Sprauer .................... 252/DIG. 18 |
| 2,760,940 | 4/1956 | Schwarzenbek ............... 252/472 |
| 3,542,863 | 11/1970 | Zimmerschred ............... 252/472 |

*Primary Examiner*—Norman Morgenstern
*Attorney, Agent, or Firm*—Michael S. Jarosz; Jack B. Murray, Jr.

[57] ABSTRACT

Palladium catalysts employed in the hydrogenation of reducible cyclic organic compounds containing deleterious nitrogen impurities are reactivated according to a process comprising separating spent catalyst from the hydrogenation reaction mixture; contacting the separated spent catalyst in a liquid reaction medium with a reactivating agent selected from the group consisting of alkali metal and alkaline earth metal bicarbonates, carbonates, nitrates, chlorides, fluorides, hydroxides and mixtures thereof, to reactivate the catalyst; and recovering the reactivated catalyst for recycle to the hydrogenation reaction mixture.

12 Claims, No Drawings

3,959,382

METHOD FOR REACTIVATING PALLADIUM CATALYSTS

BACKGROUND OF THE INVENTION

1. Field of the Invention

This invention relates to the reactivation of metallic hydrogenation catalysts and more specifically to the reactivation of palladium catalysts employed in the hydrogenation of reducible cyclic organic compounds.

2. Description of the Prior Art

In the hydrogenation of reducible cyclic organic compounds employing palladium catalysts, the presence of impurities which inhibit the desired hydrogenation reaction by poisoning the palladium catalyst is undesirable due to the uneconomical rates of hydrogenation which result from such inhibition. A class of impurities capable of inhibiting the hydrogenation of such reducible cyclic organic compounds which are especially disadvantageous are those which contain nitrogen. Such compounds, herein termed "deleterious nitrogen impurities," include, for example, ammonium salts, hydroxylamine salts, urea, tertiary amines, primary amines, and polyamines. Such impurities may be introduced into the hydrogenation reaction mixture from a variety of sources. For example, while phenol may be successfully treated by the process of U.S. Pat. No. 3,692,845 to remove carbonyl impurities prior to hydrogenation, the recovery of phenol from the purification step as by distillation may cause the inadvertent transfer of the polyamine to the recovered phenol, thereby introducing the polyamine as a deleterious nitrogen impurity into the hydrogenation reaction mixture. While processes such as that disclosed in U.S. Pat. No. 3,824,193 have been developed for reactivation of particular metallic hydrogenation catalysts employed in specific hydrogenation systems, the requirements in such processes of heating the catalyst prior to its recycle to the hydrogenation mixture is disadvantageous due to the added expense which such heating steps entail and to the possible degredation of the catalyst as a result of such heating treatments. Another process employed in the treatment of spent catalysts is that process which is described in U.S. Pat. No. 2,692,240.

SUMMARY OF THE INVENTION

According to the process of the present invention, palladium catalysts employed in the hydrogenation of reducible cyclic organic compounds containing deleterious nitrogen impurities are reactivated by separating the catalyst from the hydrogenation reaction mixture, contacting the separated catalyst in a liquid reaction medium with a reactivating agent selected from the group consisting of alkali metal and alkaline earth metal bicarbonates, carbonates, nitrates, chlorides, fluorides, hydroxides and mixtures thereof to reactivate the catalyst and recovering the reactivated catalyst. The recovered reactivated catalyst may be recycled for hydrogenation of additional reducible cyclic organic compounds.

It has been unexpectedly found that palladium catalysts poisoned with deleterious nitrogen impurities may be cheaply and efficiently reactivated by the process of the present invention wherein separated spent catalyst poisoned with deleterious nitrogen impurities is contacted with a reactivating agent selected from the group consisting of alkali metal and alkaline earth metal bicarbonates, carbonates, nitrates, chlorides, fluorides, hydroxides and mixtures thereof. By the process of the present invention, catalyst reactivation of up to 100 percent reactivation and more may be achieved. This increased reactivation is especially significant due to the large tonnages of palladium catalysts which are used annually in industry. Thus, reactivation of palladium catalysts poisoned with deleterious nitrogen compounds by the process of the present invention avoids both the economically disadvantageous rates of reaction which accompany the continued use of such spent catalyst and the need to discard such catalyst.

DETAILED DESCRIPTION OF THE INVENTION

According to the present invention, spent palladium catalysts employed in the hydrogenation of reducible cyclic organic compounds containing deleterious nitrogen impurities are reactivated by a process, which comprises: separating the spent palladium catalyst from the hydrogenation reaction mixture; contacting the separated catalyst in a liquid reaction medium with a reactivating agent selected from the group consisting of alkali metal and alkaline earth metal bicarbonates, carbonates, nitrates, chlorides, fluorides, hydroxides, and mixtures thereof, to reactivate the catalyst; and recovering the reactivated catalyst for recycle to the hydrogenation reaction mixture.

The palladium catalysts useful in the present invention contain palladium, in either its elemental or combined form, as a catalytically active metal. The palladium is generally dispersed or adsorbed on the surface of an inert support. Such supports are well know and include for example active carbon, silica, alumina, diatomaceous earth, kieselguhr and mixtures thereof. Thus, palladium catalysts which may be employed in the present invention include palladium oxide, palladium-on-carbon and palladium black. While the amount of palladium incorporated on the selected inert support may vary widely, when the selected palladium catalyst is palladium-on-carbon catalyst, the catalyst generally contains palladium in an amount of from about 0.1 to 50 weight percent, and preferably from about 0.5 to 10 weight percent, based on the total weight of the catalyst. Especially preferred as palladium catalysts in the present invention are palladium-on-carbon catalysts containing from 2 to 10 weight percent palladium. A satisfactory and commercially available catalyst contains 5 weight percent palladium-on-charcoal.

Palladium catalysts employed in the hydrogenation of reducible cyclic organic compounds are determined to be "poisoned," "inactivated" or "spent" when the rate of hydrogenation is less than the rate of hydrogenation obtained employing fresh catalyst. Thus, where for example, 113 parts by weight of cyclohexanone are produced after 2.5 hours by hydrogenating 160 parts by weight of phenol containing 5 ppm sulfur values at 185°C. and 70 psig. in the presence of 0.25 part by weight of a 5 weight percent palladium-on-carbon catalyst, the catalyst is considered to be poisoned or inactivated when the rate of hydrogenation under the same temperature and pressure conditions falls below that indicated above for fresh catalyst. Alternatively, a poisoned catalyst is determined to be "reactivated" by the process of the present invention when the treated catalyst catalyzes the hydrogenation of a selected reducible organic compound at a rate which exceeds the rate of hydrogenation achieved when the same organic compound is hydrogenated employing the poisoned or inactivated catalyst. The activity of the reactivated catalyst may therefore approach the activity of the fresh catalyst and in some cases has been found to exceed the activity of fresh catalyst. The degree of reactivation may be expressed in terms of "percent reactivation," whereby the rate of hydrogenation obtained employing reactivated catalyst is expressed as a percent of the rate of hydrogenation obtained employing fresh catalyst.

Reducible cyclic organic compounds useful in the present invention are those organic compounds which contain ring unsaturation which becomes partly or completely saturated with hydrogen during hydrogenation. Suitable reducible organic compounds include those selected from the group consisting of aromatic and unsaturated cycloaliphatic alcohols, alcohol ethers, acids and acid esters. Typical reducible cyclic organic compounds which may be employed include: aromatic alcohols of 6 to 20 carbon atoms, e.g. phenol, cresol, resorcinol and nonyl phenol; aromatic alcohol ethers of 7 to 20 carbon atoms, e.g. anisole and 2-methyl-5-ethylphenyl-n-hexyl ether; aromatic carboxylic acids of 7 to 20 carbon atoms, e.g. benzoic acid, phenylacetic acid, phthalic acid and 4-octylbenzoic acid; aromatic carboxylic acid alkyl esters of 8 to 20 carbon atoms, e.g. ethyl benzoate and pentyl phenylacetate; unsaturated cycloaliphatic alcohols of 5 to 20 carbon atoms, e.g. 3-cyclohexene-1-ol and 2-methyl-5-cyclooctene-1-ol; unsaturated cycloaliphatic alcohol esters of 6 to 20 carbon atoms, e.g. 3-cyclohexenyl (methyl) ether and 4-cyclooctenyl (isobutyl) ether; unsaturated cycloaliphatic carboxylic acids of 6 to 20 carbon atoms, e.g. 3-cyclopentenyl carboxylic acid and 5-(n-pentyl)-3-cyclooctenyl carboxylic acid; and unsaturated cycloaliphatic carboxylic acid alkyl esters of 7 to 20 carbon atoms, e.g. the methyl, butyl and heptyl esters of 3-cyclohexenyl carboxylic acid. Especially preferred reducible cyclic organic compounds in the present invention are phenol, cresol, resorcinol and other substituted phenols. The reducible cyclic organic compounds employed in the present invention should contain not greater than about 20 ppm, and preferably not greater than about 10 ppm, sulfur values (calculated as elemental sulfur); not greater than about 2 ppm, and preferably not greater than about 1 ppm iron values (calculated as elemental iron); and not greater than about 100 ppm, and preferably not greater than about 50 ppm acetol (i.e., hydroxy-2-propanone).

The process of the present invention may be employed to reactivate palladium catalysts which have been poisoned by a wide variety of deleterious nitrogen impurities, such as: ammonium salts, e.g. ammonium chloride, ammonium iodide and triammonium phosphate; hydroxylamine salts, e.g. hydroxylamine hydrochloride; urea, tertiary amines, e.g. triethylamine and dimethyl-sec-butylamine; primary amines, e.g. methylamine and n-hexylamine; and polyamines, e.g. hexamethylene diamine and hexamethylene tetraamine.

Of course, the effect which a given deleterious nitrogen impurity has upon a palladium catalyst varies widely according to the specific palladium catalyst, the conditions of temperature and pressure of hydrogenation, the concentration of the impurity and catalyst in the hydrogenation reaction mixture and other factors. The process of the present invention may be employed to reactivate palladium catalysts separated from a hydrogenation reaction mixture containing deleterious nitrogen impurities in a concentration of from about 1 to 5,000 ppm, and preferably from about 50 to 1,000 ppm.

The palladium catalyst to be reactivated according to the method of the present invention is separated from the hydrogenation reaction mixture which contains the spent catalyst, unreacted reducible cyclic organic compound and the product of the hydrogenation mixture reaction. The catalyst may be separated from the hydrogenation mixture either batchwise or continuously employing any standard solids separation procedure, such as by centrifuging, vacuum filtering or allowing the catalyst to settle and decanting the liquid. While not required, the separated spent catalyst may then be washed with fresh organic solvent to remove soluble impurities. While suitable organic solvents include alcohols, e.g. methanol, ethanol and isopropanol, and phenols, e.g. phenol and alkylated phenols (such as cresol), the solvent employed preferably corresponds to the reducible cyclic organic compound in the hydrogenation of which the spent catalyst, upon reactivation, is to be employed. The separated spent catalyst is then passed, as a solid or an an aqueous organic solvent slurry of catalyst, to a contacting vessel wherein the catalyst is contacted with the selected alkali metal compound.

The reactivating agents which may be employed in reactivating spent palladium catalysts in accordance with the present invention are those selected from the group consisting of alkali metal and alkaline earth metal bicarbonates, carbonates, nitrates, chlorides, fluorides, hydroxides and mixtures thereof. Preferred reactivating agents are those selected from the group consisting of alkali metal bicarbonates, carbonates, alkali metal nitrate and mixtures thereof. Especially preferred reactivating agents are sodium carbonate, sodium bicarbonate, sodium nitrate and mixtures thereof.

The selected reactivating agent and the spent catalyst are contacted in a liquid medium which may comprise either an aqueous or organic solvent medium. Preferably, where the catalyst is passed to the contacting vessel as either an aqueous or organic solvent slurry, the liquid medium in which the reactivating agent and catalyst are contacted corresponds to that which is used to slurry the catalyst for transfer to the contacting vessel. Suitable organic solvents include aromatic and unsaturated cycloaliphatic alcohols, alcohol ethers, acids and acid esters. Typical organic solvents which may be employed are those classes of compounds disclosed above as typical of the reducible cyclic organic compounds which may be hydrogenated. The organic solvent preferably corresponds to that reducible cyclic organic compound which is to be hydrogenated employing the reactivated catalyst.

The precise amount of reactivating agent to be added to the contacting vessel to effect of the catalyst depends on the particular reactivating agent employed, the amount of palladium in the catalyst to be reactivated, the temperature, the degree of reactivation desired and other factors. Generally, however, the selected reactivating agent is added to the contacting vessel in an amount of from about 0.01 to 10, and preferably 0.1 to 2, grams of reactivating agent per gram of palladium.catalyst to be reactivated. When the catalyst and reactivating agent are contacted in aqueous medium and when an alkali metal or alkaline earth metal bicarbonate, carbonate or hydroxide is employed, the selected alkali metal or alkaline earth metal compound is preferably added to the contacting vessel in an amount which effects a pH greater than 7, and most preferably a pH of from about 8 to 10, for the most efficient reactivation of the palladium catalyst.

In order to effect reactivation of the spent palladium catalyst in accordance with the process of the present invention, the spent catalyst and reactivating agent should be contacted at a temperature of at least about 150°C, preferably at least 170°C.

After the separated spent catalyst and reactivating agent are added to the contacting vessel for reactivation of the catalyst, the vessel is sealed and the reactivation mixture, e.g. the liquid medium containing the catalyst and reactivating agent, is heated to the desired temperature under autogenous pressure. The term "autogenous pressure" is herein meant to define the pressure at which the vapor and liquid phases of the catalyst-reactivating agent mixture are in equilibrium at the selected temperature. Of course, this pressure varies depending upon the temperature employed, the particular reactivating agent and its concentration in the solution, and other factors, but is generally from 50 to 300 psig.

The time for which the reactivation mixture is maintained at the above temperature and pressure to effect reactivation of the catalyst varies according to the catalyst being reactivated, the reactivating agent selected for use, the the relative amounts of catalysts and reactivating agent admixed, the degree to which the catalyst has been poisoned and other factors, but is generally from about 0.2 to about 2 hours. Thus, for example, where 0.25 grams of a palladium-on-carbon catalyst containing 5.0 weight percent palladium, which has been poisoned with 1100 ppm hexamethylenediamine, is contacted at a temperature of 180°C. and a pressure of 150 psig. with 80 ml. of 0.31 weight percent aqueous solution of alkali metal carbonate, 2 hours are required to effect 116 percent reactivation of the catalyst.

The contacting vessel may be any vessel capable of withstanding the above conditions of temperature and pressure and composed of a material which is non-reactive with the components of the reactivation mixture. Such contacting vessels are conventional and include liquid plug flow reactors and vessels capable of being hermetically sealed. The contacting vessel may be heated by any suitable heating means, such as by external steam heating coils, induction heating and the like. Agitation of the reactivation mixture may also be employed to increase the rate at which the catalyst is reactivated. Such agitation may be effected by standard agitation devices such as by rotational mixing.

After the catalyst has been contacted in the contacting vessel with the selected reactivating agent for the desired period of time, the reactivated catalyst is separated from the reactivation mixture for recycle to the hydrogenation reaction mixture. Any standard separation procedures may be employed to remove the catalyst from the mixture, such as filtration, vacuum filtration centrifugation and the like. While not required, it is preferred to wash the separated reactivated catalyst with fresh reducible cyclic organic compound so as to remove the reactivating agent therefrom prior to the addition of the rectivated catalyst to the hydogenation reaction mixture. For those hydrogenation reactions for which the presence of water is detrimental, e.g. the hydrogenation of phenol to cyclohexanone, the reactivated catalyst may also be dried such as by vacuum filtration to remove substantially all water therefrom prior to recycling the catalyst. The alkali metal compound which remains after the reactivated catalyst is separated from the reactivation mixture may be recycled with the optional addition of make-up reactivating agent to the contacting vessel for subsequent treatment of additional spent palladium catalyst.

The process of the present invention may be further illustrated by reference to the following examples wherein parts are by weight unless otherwise indicated.

EXAMPLE 1

To determine the activity of fresh palladium catalysts, 160 parts of phenol containing 7 ppm sulfur values (calculated as elemental sulfur) and 0.1 ppm iron values (calculated as elemental Fe) is admixed with 0.25 part 5 weight percent palladium-on-carbon catalyst, and the resulting mixture introduced into a stainless steel Magne Drive autoclave. Gaseous hydrogen is then introduced into the reactor and the mixture is hydrogenated at a temperature of 185°C. and a pressure of 70 psig. After 150 minutes, the hydrogenation reaction mixture is determined to contain 69.2 percent by weight cyclohexanone.

To determine the percent reactivation effected by the process of the present invention, 0.25 part of fresh 5% palladium-on-carbon catalyst is intentionally poisoned by admixing the fresh catalyst with 160 parts of phenol containing 7 ppm sulfur values and 0.1 ppm iron values to which is added 1,100 hexamethylenediamine as deleterious nitrogen impurity. The resulting mixture is charged to a Magne Drive autoclave and hydrogenated at a temperature of 185°C. and a pressure of 70 psig. for a period of 2.5 hours. At the end of the above period the catalyst, poisoned with the above deleterious nitrogen impurity, is isolated by vacuum filtration and is passed to a second Magne Drive autoclave for hydrogenation of a second phenol portion. No catalyst activity for phenol reduction cyclohexanone is found for the poisoned catalyst.

Vacuum filtration is then employed to isolate 0.25 part of the catalyst poisoned as above. The isolated catalyst is slurried with 80 parts of water containing 0.25 parts sodium carbonate to yield an aqueous sodium carbonate solution having a pH of 8. This solution is then heated in a Magne Drive autoclave to a temperature of 185°C. and autogenous pressure (155 psig.) for a period of two hours. At the end of the above period, the mixture is allowed to cool to room temperature and the catalyst is recovered by filtration. The recovered catalyst is slurried with 80 parts of pure phenol and again filtered to remove substantially all water therefrom. A 0.2 part portion of the catalyst thus isolated is passed to a Magne Drive autoclave and is employed to hydrogenate phenol to cyclohexanone following the process described in paragraph 1 above. After 150 minutes, the hydrogenation reaction mixture is found to contain 80.8 weight percent cyclohexanone. Thus, catalyst reactivated according to the process of the present invention effects about an 18 percent increase in cyclohexanone production.

Similar results are obtained in separate runs employing sodium hydroxide, sodium nitrate and sodium chloride, respectively, as the reactivating agent.

Although certain preferred embodiments of the invention have been disclosed for the purpose of illustration it will be evident to one skilled in the art that various changes and modifications may be made therein without departing from the scope and spirit of the invention.

We claim:

1. A process for the reactivation of the spent palladium catalyst employed in the hydrogenation of reducible cyclic organic compound containing deleterious nitrogen impurities in a concentration of from about 1 to 5,000 ppm which comprises: separating the spent catalyst from the hydrogenation reaction mixture; and contacting said separated spent catalyst in a liquid reactivation medium at a temperature of at least about 150°C with a reactivating agent selected from the group consisting of alkali metal and alkaline earth metal bicarbonates, carbonates, nitrates, chlorides, fluorides, hydroxides and mixtures thereof to reactivate the catalyst.

2. The process according to claim 1 wherein said reactivation agent is employed in an amount of from about 0.01 to 10 grams reactivating agent per gram of said separated spent catalyst.

3. The process accorrding to claim 1 wherein said deleterious nitrogen impurities include impurities selected from the group consisting of ammonium salts, hydroxylamine salts, urea tertiary amines, primary amines and polyamines.

4. The process according to claim 1 wherein said reducible cyclic organic compound comprises phenol.

5. The process according to claim 1 wherein said reducible cyclic organic compound contains not greater than about 20 ppm sulfur values (calculated as elemental sulfur), not greater than about 2 ppm iron values (calculated as elemental iron) and not greater than about 100 ppm acetol.

6. The process according to claim 5 wherein said liquid medium comprises an aqueous medium.

7. The process according to claim 5 wherein said liquid medium comprises an organic solvent.

8. The process according to claim 7 wherein said organic solvent is selected from the group consisting of aromatic and unsaturated cycloaliphatic alcohols, alcohol ethers, acids and acid esters.

9. The process according to claim 6 wherein said reactivating agent is selected from the group consisting of alkali metal hydroxides, carbonates, and mixtures thereof and wherein said reactivating agent is employed in said aqueous medium in an amount sufficient to effect a pH greater than 7.

10. The process according to claim 5 wherein said reactivated catalyst is separated from the liquid reactivation medium and recycled for hydrogenation of additional reducible cyclic organic compound.

11. The process according to claim 5 wherein said palladium catalyst is palladium-on-carbon catalyst.

12. The process according to claim 5 wherein said reducible cyclic organic compound is a member selected from the group consisting of aromatic and unsaturated cycloaliphatic alcohols, alcohol ethers, acids and acid esters.

* * * * *